(12) United States Patent
Yamamoto et al.

(10) Patent No.: US 7,682,831 B2
(45) Date of Patent: Mar. 23, 2010

(54) METHOD OF MEASURING LIPID IN SPECIFIC LIPOPROTEIN

(75) Inventors: Shoko Yamamoto, Ibaraki (JP); Mitsuaki Yamamoto, Ibaraki (JP); Kazuo Nakanishi, Ibaraki (JP); Kazunori Saito, Ibaraki (JP)

(73) Assignee: Sekisui Medical Co., Ltd., Tokyo (JP)

(*) Notice: Subject to any disclaimer, the term of this patent is extended or adjusted under 35 U.S.C. 154(b) by 1211 days.

(21) Appl. No.: 10/536,186

(22) PCT Filed: Nov. 26, 2003

(86) PCT No.: PCT/JP03/15080

§ 371 (c)(1), (2), (4) Date: May 24, 2005

(87) PCT Pub. No.: WO2004/048605

PCT Pub. Date: Jun. 10, 2004

(65) Prior Publication Data

US 2006/0014207 A1 Jan. 19, 2006

(30) Foreign Application Priority Data

Nov. 27, 2002 (JP) ............................ 2002-343979
Nov. 28, 2002 (JP) ............................ 2002-346115

(51) Int. Cl.
*G01N 33/92* (2006.01)

(52) U.S. Cl. ........................... 436/71; 436/63; 436/175; 435/11; 435/19

(58) Field of Classification Search ............... 436/8, 436/13, 63, 71, 174, 175; 435/11, 19, 7.1; 252/408.1
See application file for complete search history.

(56) References Cited

U.S. PATENT DOCUMENTS

| 4,892,815 A * | 1/1990 | Kerscher et al. ............. 435/7.1 |
| 5,814,472 A | 9/1998 | Miki et al. |
| 6,057,118 A * | 5/2000 | Nakamura et al. ............ 435/11 |
| 6,479,249 B2 | 11/2002 | Matsui et al. |
| 6,939,682 B2 * | 9/2005 | Tamura et al. ................ 435/11 |
| 7,202,047 B2 * | 4/2007 | Miyauchi ..................... 435/11 |

FOREIGN PATENT DOCUMENTS

| EP | 0 764 848 A1 | 3/1997 |
| EP | 0 913 484 A1 | 5/1999 |
| EP | 0 990 904 A1 | 4/2000 |
| EP | 1 020 532 A1 | 7/2000 |
| EP | 1 046 716 A1 | 10/2000 |
| EP | 1 132 482 A2 | 9/2001 |
| EP | 1 148 142 A1 | 10/2001 |
| EP | 1 158 299 A1 | 11/2001 |
| EP | 1 498 732 A2 | 1/2005 |
| EP | 1 505 393 A1 | 2/2005 |
| EP | 1 555 326 A1 | 7/2005 |
| JP | 63-126498 | 5/1988 |
| JP | 6-242110 | 9/1994 |
| JP | 7-301636 | 11/1995 |
| JP | 8-322596 | 12/1996 |
| JP | 9-299 | 1/1997 |
| JP | 2600065 | 1/1997 |
| JP | 9-96637 | 4/1997 |
| JP | 9-313200 | 12/1997 |
| JP | 10-38888 | 2/1998 |
| JP | 11-56395 | 3/1999 |
| JP | 11-318496 | 11/1999 |
| JP | 2000-116400 | 4/2000 |
| JP | 2001-103998 | 4/2001 |
| JP | 2002-142799 | 5/2002 |
| JP | 2002-214239 | 7/2002 |
| WO | WO 81/01199 | 4/1981 |
| WO | 96/28734 | 9/1996 |
| WO | 96/29599 | 9/1996 |
| WO | 97/45553 | 12/1997 |
| WO | 99/10526 | 3/1999 |
| WO | WO 99/31512 | 6/1999 |
| WO | 00/43537 | 7/2000 |
| WO | WO 00/60112 | 10/2000 |
| WO | 02/38800 | 5/2002 |

OTHER PUBLICATIONS

Derwent Publications LTD., JP 59-091897, AN-1984-168215, XP002425361, May 26, 1984, 1 Page.

M. Okada, et al., "Low-density lipoprotein cholesterol can be chemically measured: A new superior method", Journal of Laboratory and Clinical Medicine, XP001084725, vol. 132, No. 3, Sep. 3, 1998, pp. 195-201.

Taro Sakaue, et al., "Reactions of direct LDL-cholesterol assays with pure LDL fraction and IDL: comparison of three homogeneous methods", Clinica Chimica Acta, XP002425351, vol. 295, No. 1-2, May 2000, pp. 97-106.

K. R. Kulkarni, et al., "Quantification of cholesterol in all lipoprotein classes by the VAP-II method", Journal of Lipid Research, XP002425351, vol. 35, No. 1, Jan. 1994, pp. 159-168.

Kao Corporation, "Nonionic surfactants—"Polyoxyethylene derivatives"" [Online], XP002425353, Mar. 1999, 2 Pages.

Database Registry, "Emulgen A 90, Emulgen A 60", American Chemical Society, Nov. 16, 1984, XP002425354, Database accession No. 9086-52-6, 1 Page.

Database Registry, "Emulgen B 66", American Chemical Society, XP002425355, Nov. 16, 1984, Accession No. 68310-58-7, 1 Page.

U.S. Appl. No. 11/305,355, filed Dec. 19, 2005, Nakanishi, et al.

* cited by examiner

*Primary Examiner*—Maureen M Wallenhorst
(74) *Attorney, Agent, or Firm*—Oblon, Spivak, McClelland, Maier & Neustadt, L.L.P.

(57) ABSTRACT

A method of measuring a lipid in a specific lipoprotein characterized by using a polycyclic polyoxyalkylene derivative at least in the step of determining the specificity of the measurement of the target lipid.

14 Claims, 4 Drawing Sheets

METHOD OF MEASURING LIPID IN SPECIFIC LIPOPROTEIN

TECHNICAL FIELD

The present invention relates to a method for efficiently separating and assaying a lipid contained in a specific fraction by means of a simple operation employing a small amount of a sample; and to a reagent employed for the method.

BACKGROUND ART

Cholesterol, triglyceride, and phospholipid are bound to apoproteins in blood plasma to form lipoproteins. In accordance with their physical properties, lipoproteins are classified into, for example, chylomicron, very low density lipoprotein (VLDL), low density lipoprotein (LDL), and high density lipoprotein (HDL). In some cases, LDL is further classified into intermediate density lipoprotein (IDL) and LDL. A product obtained through decomposition of lipoprotein; i.e., a remnant, is occasionally considered a type of lipoprotein. Of these lipoproteins, LDL is known to be a substance that induces arteriosclerosis, whereas HDL is known to exhibit anti-arteriosclerotic activity.

Epidemiologically, the level of apoproteins or cholesterol in LDL is known to exhibit a positive correlation with the frequency of onset of arteriosclerotic diseases, whereas the level of apoproteins or cholesterol in HDL is known to exhibit an inverse correlation with the frequency of onset of arteriosclerotic diseases. Therefore, nowadays, apoproteins or cholesterol contained in LDL or HDL is assayed for the purpose of prevention or diagnosis of ischemic heart diseases.

Known methods for assaying lipids contained in LDL or HDL include a method in which LDL or HDL is separated from other lipoproteins by means of ultracentrifugation, and is then subjected to lipid assay; and a method in which LDL or HDL is separated from other lipoproteins by means of electrophoresis, and is then subjected to lipid staining, followed by measurement of the intensity of coloring. However, these methods have hardly been practiced for problems accompanied by each of the methods such as a requirement for intricate procedures and a difficulty in handling a large number of samples.

Among assays of lipids contained in lipoproteins, HDL cholesterol assays are performed most frequently. In clinical examinations, HDL cholesterol is usually assayed by the precipitation method, in which a precipitant is added to a sample to thereby aggregate lipoproteins other than HDL, then the thus-aggregated lipoproteins are removed through centrifugation, and cholesterol in the thus-separated supernatant containing only HDL is assayed. However, this method requires a relatively large amount of sample, and complete automation of entire analytical steps has not been accomplished. In recent years, there have been proposed a variety of methods that enzymatically separate and assay HDL cholesterol. Examples of such methods include a method employing enzymatic reaction in the presence of a bile salt and a nonionic surfactant (JP-A-63-126498); a method in which lipoproteins other than HDL are aggregated in advance so that HDL cholesterol is only reacted with an enzyme, and subsequently the enzyme is inactivated while the aggregated lipoproteins are re-dissolved simultaneously, followed by measurement of absorbance (JP-A-6-242110); a method employing a precipitant which precipitates lipoproteins other than HDL and a cholesterol assay reagent in combination, in which cholesterol contained in non-precipitated HDL is assayed (JP-B-2600065); a method employing an antibody (JP-A-9-96637); a method employing a sugar compound (JP-A-7-301636); a method in which, in a first reaction, cholesterol oxidase and cholesterol esterase act on lipoproteins other than HDL in the presence of a specific surfactant, to thereby preferentially react these enzymes with cholesterol contained in these lipoproteins, and subsequently HDL cholesterol is assayed while inhibiting any reaction with cholesterol contained in the lipoproteins other than HDL (JP-A-9-299); a method employing a surfactant selected from a specific group and a cholesterol assay enzyme reagent, in which HDL cholesterol is assayed within a period of time when the enzyme reagent is preferentially reacted with the cholesterol contained in HDL (JP-A-11-56395); and a method employing cholesterol oxidase and cholesterol esterase in combination with a surfactant which acts specifically on HDL cholesterol (JP-A-2001-103998).

Clinical significance of an LDL cholesterol assay—which is also commonly performed next to HDL cholesterol—is widely known through large-scale epidemiological studies; however, a method for assaying LDL cholesterol (e.g., a method such as the aforementioned precipitation method for assaying HDL cholesterol) has not been developed. For this reason the LDL cholesterol has been assayed by means of a conversion method (the Freidewald method, hereinafter abbreviated as the "F method") which calculates an "estimate" on the basis of the results of the ultracentrifugation method. In the case of the F method, the LDL cholesterol level is calculated by subtracting the HDL cholesterol level and the VLDL cholesterol level from the total cholesterol level, where a ⅕ value of the triglyceride level is employed as the VLDL cholesterol level. Since the VLDL cholesterol level is estimated from the triglyceride level, the F method cannot be applied to a patient having a triglyceride level of more than 400 mg/dl or a patient with type III hyperlipidemia. Another problem entailed by the F method is that the assay data are negatively biased when the subject exhibits a transient increase in triglyceride level due to meal intake. In view of the foregoing, there have been developed enzymatic methods for assaying LDL cholesterol, including a method in which HDL cholesterol is eliminated from a sample containing LDL cholesterol, and the remaining LDL cholesterol is assayed (JP-A1-8-828734); and a method in which LDL cholesterol in a sample is assayed in the presence of a sugar compound and/or a protein solubilizing agent (JP-A1-8-829599). Furthermore, there have been proposed a method employing a surfactant having a specific structure (JP-A-9-313200) and a method employing a surfactant which acts on lipoproteins other than LDL in a buffer solution containing an amine (JP-A-10-38888).

In blood plasma, most of the triglyceride exists as VLDL. Therefore, in estimation of the LDL cholesterol level by means of the aforementioned F method, the triglyceride level is employed for estimating the VLDL cholesterol level (VLDL cholesterol level=TG/5). In general, the triglyceride is assayed by means of a method in which free glycerol is consumed in a first reaction, and then free glycerol generated by lipoprotein lipase is phosphorylated in a second reaction, and glycerophosphate oxidase is applied thereon, then the thus-generated hydrogen peroxide is reacted with peroxidase, 4-aminoantipyrine, and a Trinder dye for coloring. Consumption of free glycerol is determined by means of so-called achromatic color appearance method employing either peroxidase and a substrate thereof or catalase, or a combination thereof. Methods conventionally known for assaying triglyceride contained in a specific lipoprotein include a fractionation method employing ultracentrifugation or an aggregating agent; and a fractionation method employing gel filtration. There has also been disclosed a method employing a surfactant which inhibits reaction of lipoproteins other than a specific lipoprotein, or a surfactant having an HLB of 15 or more (International Publication WO 00/43537).

DISCLOSURE OF THE INVENTION

Those additives conventionally employed have not been satisfactory, from the viewpoints of, for example, their specificity to a specific lipoprotein, and their effects on the activity of an enzyme employed for lipid assay. In order to search for an additive which meets certain requirements, at least HDL, LDL, and VLDL, all of which are major lipoproteins, need to be separated and prepared from fresh human blood by use of an expensive apparatus (e.g., an ultracentrifugation apparatus), and each of the thus-prepared lipoproteins further needs to go through evaluation and selection. This procedure requires considerable time and cost.

In view of the foregoing, an object of the present invention is to provide a method for efficiently assaying a lipid contained in a specific fraction through a simple operation, which method can be applied to a variety of automatic analyzers.

The present inventors have conducted extensive studies, and as a result have found that when specific surfactants are employed at least in a step of determining the specificity of an assay for a target lipid contained in a specific lipoprotein in a sample, the target lipid can be specifically assayed; and that the surfactants have a common structural feature. The present invention has been accomplished on the basis of these findings.

Accordingly, the present invention provides a method for assaying a lipid contained in a specific lipoprotein, which method comprises a step of determining the specificity of an assay for a target lipid contained in a specific lipoprotein, wherein a polycyclic polyoxyalkylene derivative is employed at least in the specificity determining step.

The present invention also provides a reagent for assaying a lipid contained in a specific lipoprotein, which reagent comprises a polycyclic polyoxyalkylene derivative which acts on a specific lipoprotein, and a reagent for assaying a target lipid (hereinafter the reagent may be referred to as a "target lipid assay reagent").

According to the present invention, a useful surfactant can be efficiently selected from among various surfactants, and, by use of the thus-selected surfactant, a target lipid contained in a specific fraction can be efficiently quantified by means of a simple operation without pretreatment (e.g., centrifugation) of the fraction. The method of the present invention enables specific assay of a target lipid through a simple operation with minimized sample amount so that it can be applied to various analytical techniques, thus is also very useful in the field of clinical testing.

BEST MODE FOR CARRYING OUT THE INVENTION

Figure 1:
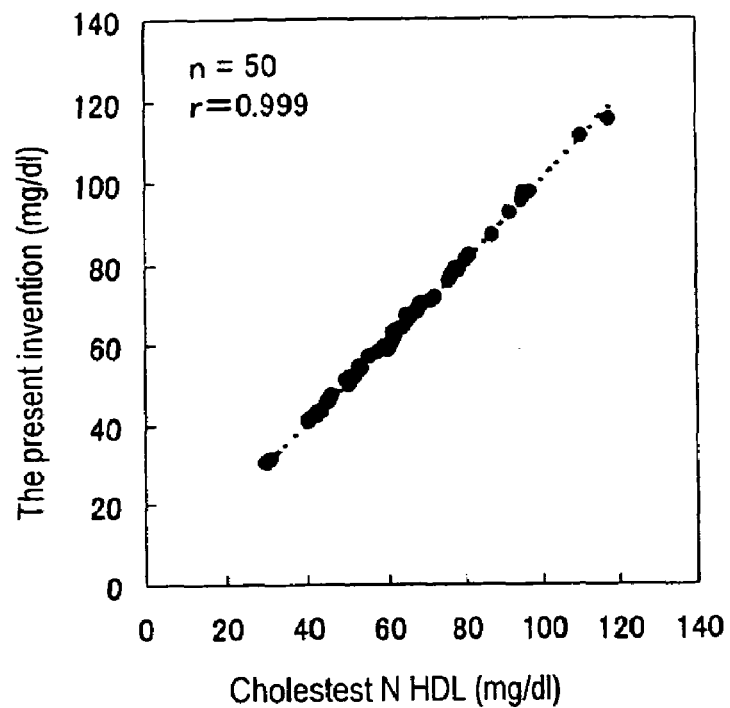
FIG. 1 shows the correlation between the method of the present invention and a conventional method (by use of Cholestest N HDL).

Examples of the polycyclic polyoxyalkylene derivative employed in the present invention include nonionic or anionic surfactants having a polycyclic group; i.e., a group formed of two or more aryl groups. Examples of the aryl group include a phenyl group, a naphthyl group, an alkylphenyl group, a phenylalkyl group, and a phenylalkenyl group. Examples of the alkylphenyl group include $C_1$-$C_{20}$ alkylphenyl groups such as a nonylphenyl group. Examples of the phenylalkyl group include phenyl-$C_1$-$C_6$ alkyl groups such as a benzyl group. Examples of the phenylalkenyl group include phenyl-$C_2$-$C_6$ alkenyl groups such as a styryl group. The number of such aryl groups is preferably 2 to 10, particularly preferably 2 to 8, but is not limited to such a number in the case of a condensate.

Preferred examples of the polycyclic group include a polycyclic group comprising a phenyl group substituted by one to five (preferably one to three) aryl groups selected from among a phenyl group, a naphthyl group, an alkylphenyl group, a phenylalkyl group, and a styryl group.

Examples of the polyoxyalkylene group constituting the surfactant include a polyoxyethylene group, a polyoxyethylene-polyoxypropylene group, and a polyoxypropylene group. Of these, a polyoxyethylene group is particularly preferred. The polyoxyalkylene addition mole number, which varies depending on the target lipid to be assayed and the type of the polyoxyalkylene group, is preferably 2 to 100, more preferably 5 to 50, particularly preferably 10 to 50.

Of the polycyclic polyoxyalkylene derivatives, the nonionic surfactant is preferably a polyoxyalkylene ether-type nonionic surfactant. In the case of a nonionic surfactant, one having an HLB of 12 to 18 is preferably employed. Preferable anionic surfactants include a sulfonic ester-type, phosphoric ester-type, or sulfosuccinate-type.

When the target lipid is cholesterol, the polycyclic polyoxyalkylene derivative to be employed is preferably a nonionic surfactant which acts on a specific lipoprotein and has an HLB of 12 to 18, where the specificity of the surfactant to the target lipid does not depend on the HLB of the surfactant but is affected entirely by the number of aryl groups contained in the surfactant.

When the target lipid is cholesterol, the polycyclic polyoxyalkylene derivative to be employed is preferably a nonionic surfactant which acts on a specific lipoprotein and has an HLB of 12 to 18, and further contains two or more aryl groups (exclusive of a surfactant having an HLB of 13 to 15, whose specificity to assay of cholesterol in LDL is affected by the buffer solution).

When the target lipid is cholesterol in HDL, the polycyclic polyoxyalkylene derivative to be employed is preferably a nonionic surfactant which acts preferentially on HDL and has an HLB of 14.1 to 18 (particularly preferably an HLB of 14.3 to 18). When the target lipid is cholesterol in LDL, the polycyclic polyoxyalkylene derivative to be employed is preferably a nonionic surfactant which acts preferentially on lipoproteins other than LDL and has an HLB of 15.1 to 18 (particularly preferably an HLB of 15.3 to 18). When the target lipid is triglyceride contained in a specific lipoprotein, the polycyclic polyoxyalkylene derivative to be employed is preferably a nonionic surfactant which acts preferentially on lipoproteins other than LDL, and has an HLB of 12 to 18, and further contains two or more aryl groups. When the target lipid is triglyceride contained in LDL, the polycyclic polyoxyalkylene derivative to be employed is preferably a nonionic surfactant which acts preferentially on lipoproteins other than LDL, and has an HLB of 12 to 15, and further contains two or more aryl groups. As used herein, the expression "a surfactant acts preferentially on" refers to the case where a surfactant acts on a specific lipoprotein more preferentially than other lipoprotein.

Particularly preferred examples of the polyoxyalkylene derivative include polyoxyalkylene polycyclic phenyl ether, polyoxyethylene tribenzylphenyl ether, polyoxyalkylene polystyrylphenyl ether, polyoxyalkylene phenylphenol ether, a polyoxyalkylene polystyrylphenyl ether condensate, a polyoxyalkylene alkylphenyl ether condensate, polyoxyalkylene distyrenated phenyl ether, polyoxyalkylene styrylated phenyl ether, polyoxyalkylene allylphenyl ether, and polyoxyalkylene polycyclic phenyl sulfosuccinate, and these contain plural phenyl groups.

Examples of commercially available products of these polyoxyalkylene derivatives include polyoxyalkylene polycyclic phenyl ether products, such as Pegnol 005 (HLB: 14.6, product of Toho Chemical Industry Co., Ltd.), and Newcol 610 (HLB: 13.8), Newcol 710 (HLB: 13.6), Newcol 710F (HLB: 13.5), Newcol 714 (HLB: 15.0), Newcol 714F (HLB: 14.4), Newcol 740 (HLB: 17.9), Newcol 2600FB (HLB: 13.4), Newcol 2608F (HLB: 13.0), and Newcol 2609 (HLB: 13.0), which are products of Nippon Nyukazai Co., Ltd.; polyoxyalkylene polystyrylphenyl ether products, such as Pionin D-6112W (HLB: 13.0), Pionin D-6115X (HLB: 14.5), and Pionin D-6115Z (HLB: 15.5), which are products of Takemoto Oil & Fat Co., Ltd.; polyoxyalkylene phenylphenol ether products, such as Sorpol T-15 (HLB: 12.0), Sorpol T-20 (HLB: 13.3), and Sorpol T-26 (HLB: 14.4), which are products of Toho Chemical Industry Co., Ltd.; polyoxyalkylene polystyrylphenyl ether condensate, such as Pionin D-6320 (HLB: 13.0, product of Takemoto Oil & Fat Co., Ltd.); polyoxyalkylene alkylphenyl ether condensate, such as Pionin D-640 (HLB: 14.3, product of Takemoto Oil & Fat Co., Ltd.) and R-1020 (HLB: 18.0, product of Nikko Chemicals Co., Ltd.); polyoxyalkylene distyrenated phenyl ether products, such as Emulgen A-90 (HLB: 14.5, product of Kao Corporation); polyoxyalkylene styrylated phenyl ether products, such as Sanmol 2SP-180 (HLB: 14.5, product of Nicca Chemical Co., Ltd.) and TSP-16 (HLB: 12.7, product of Aoki Oil Industrial Co., Ltd.); polyoxyalkylene allylphenyl ether products, such as Newkalgen FS-12 (HLB: 13, product of Takemoto Oil & Fat Co., Ltd.); and polyoxyalkylene polycyclic phenyl sulfosuccinate products, such as Airrol T-1500 (product of Toho Chemical Industry Co., Ltd.).

These polycyclic polyoxyalkylene derivatives may be employed singly or by mixture, or may be employed in combination with a surfactant other than the surfactants. The polycyclic polyoxyalkylene derivative employed in the present invention may be a mixture of a plurality of polycyclic polyoxyalkylene derivatives. For example, when the polycyclic polyoxyalkylene derivative is a benzyl-group-containing phenyl ether, the phenyl ether may singly be a monobenzyl form, a dibenzyl form, or a tribenzyl form, or may be a mixture thereof. Meanwhile, when the polycyclic polyoxyalkylene derivative is a styryl-group-containing phenyl ether, the phenyl ether may singly be a monostyryl form, a distyryl form, or a tristyryl form, or may be a mixture thereof. No particular limitations are imposed on the mixing proportions of the mono-form, di-form, and tri-form, but preferably, the mixing proportions of the mono-form, di-form, and tri-form are 1 to 20%, 10 to 40%, and 40 to 90%, respectively. More preferably, the mixing proportions of the mono-form, di-form, and tri-form are 2 to 15%, 10 to 40%, and 50 to 90%, respectively. Examples of commercial products of such a mixture include Pegnol 005 (in which the approximate mixing proportions of the mono-form, di-form, and tr-form are 7%, 20%, and 73%, respectively). No particular limitations are imposed on the amount of such a derivative to be employed as it varies depending on the type of the derivative, but it is employed at 0.0001 weight % to 10 weight % (hereinafter "weight %" will be referred to simply as "%"), preferably 0.001% to 5%. In the present invention, the polycyclic polyoxyalkylene derivative is employed at least in a step of determining the specificity of the assay for a target lipid.

The present invention provides a method for assaying a target lipid contained in a specific lipoprotein; and a reagent employed for the method. Examples of the specific lipoprotein include HDL, LDL, IDL, VLDL, chylomicron, and a decomposition product thereof. Examples of the target lipid include cholesterol, triglyceride, and phospholipid. Therefore, specific examples of the target lipid to be assayed include cholesterol in HDL, cholesterol in LDL, cholesterol in VLDL, cholesterol in IDL, cholesterol in chylomicron, cholesterol in a decomposition product thereof, triglyceride in HDL, triglyceride in LDL, triglyceride in VLDL, triglyceride in IDL, triglyceride in chylomicron, triglyceride in a decomposition product thereof, phospholipid in HDL, phospholipid in LDL, phospholipid in VLDL, phospholipid in IDL, phospholipid in chylomicron, and phospholipid in a decomposition product thereof. Most of these target lipids are highly related to arteriosclerotic diseases, and thus separation and assay of the lipids are highly needed.

The method of the present invention includes a step of assaying a target lipid, and a step of determining the specificity of the assay for the target lipid. These steps may be performed separately one after the other, or simultaneously. So long as these steps proceed in a reaction system, reagent and the like are not necessarily employed stepwise in these steps. Examples of the step of determining the specificity of target lipid assay include a step of pretreating lipoproteins other than a specific lipoprotein; and a step of reacting, with an enzyme for assay, a target lipid in a target lipoprotein contained in a pretreated reaction mixture. The target lipid assay step employs a reagent for assaying the target lipid, and the assay reagent contains an enzyme that acts to release the target lipid from a lipoprotein, and example thereof includes esterase.

Examples of the sample to be employed include body fluids and body components of animals (in particular, mammals) including human. Whole blood, serum, plasma, spinal fluid, sweat, urine, lacrimal fluid, saliva, skin, and mucosa are preferred, with serum and plasma being particularly preferred. The sample may be directly employed, or may be diluted before use. Alternatively, the sample may be subjected to separation by use of an apparatus for separation, or subjected to drying.

When, for example, the target lipid is a lipid contained in HDL, "lipoproteins other than the specific lipoprotein" refer to lipoproteins other than HDL; i.e., LDL, VLDL, IDL, chylomicron, and a decomposition product thereof. When the specific lipoprotein is LDL, "lipoproteins other than the specific lipoprotein" refer to HDL, VLDL, IDL, chylomicron, and a decomposition product thereof. The surfactant of the present invention may exhibit higher affinity, or contrary lower affinity, to a specific lipoprotein than to a lipoprotein other than the specific lipoprotein so that it may be selected depending on the type of the target lipid.

In the present invention, the esterase employed in the target lipid assay reagent, which is employed for assaying a lipid constituting a lipoprotein, may be any esterase so long as it is an esterase which acts on cleaving an ester linkage, and examples thereof include cholesterol esterase, lipoprotein lipase, or phospholipid lipase. Such an esterase may be derived from, for example, microorganisms, animals, or plants, or may be prepared through genetic manipulation. Such an esterase may be chemically modified. Such an esterase may be in a solution form or in a dry form, or may be supported with or bound to an insoluble carrier.

If desired, such an esterase may be employed in combination with an enzyme other than the esterase, a coenzyme, or a color coupler, for the purpose of assay of the target lipid. Examples of the enzyme other than the esterase include cholesterol dehydrogenase, cholesterol oxidase, glycerol kinase, glycerol phosphate oxidase, glycerol phosphate dehydrogenase, glycerol dehydrogenase, pyruvate kinase, lactate dehydrogenase, choline oxidase, alkaline phosphatase, peroxidase, catalase, and diaphorase. Such an enzyme may be derived from, for example, microorganisms, animals, or plants, or may be prepared through genetic manipulation. Such an enzyme may be chemically modified. Such an enzyme may be in a solution form or in a dry form, or may be supported with or bound to an insoluble carrier. Examples of the coenzyme include nicotinamide adenine dinucleotide (NAD), reduced nicotinamide adenine dinucleotide (NADH), nicotinamide adenine dinucleotide phosphate (NADP), reduced nicotinamide adenine dinucleotide phosphate (NADPH), thio-NAD, and thio-NADP. The color coupler may be any agent, so long as it forms a dye through the effect of POD or diaphorase. Examples of the color coupler which may be employed include 4-aminoantipyrine, Trinder dye, and formazan dye. These enzymes may be employed singly or in combination of two or more species. No particular limitations are imposed on the amount of such an enzyme to be employed as it varies depending on the type thereof, but the amount of the enzyme to be employed is 0.001 units/mL to 1,000 units/mL, preferably 0.1 units/mL to 1,000 units/mL. The aforementioned two steps of the method of the present invention may be carried out separately or by use of the same reagent.

In order to adjustment the enzymatic activity without affecting the assay specificity, the enzyme-containing reagent of the present invention may contain an enzyme other than the aforementioned enzymes, a salt, a buffer for pH adjustment, a surfactant, an antiseptic, a protein (e.g., albumin), an antibiotic, saponin, lectin, a polyanion (e.g., a phosphotungstic acid salt, dextran sulfate, polyvinyl sulfate, or sulfated cyclodextrin), a divalent metal salt, polyethylene glycol, a reagent exhibiting affinity to a specific lipoprotein (e.g., phospholipid), and an azide salt serving as an antiseptic or a catalase inhibitor. Of these additives, a polyanion or a divalent metal salt which is a component for controlling the reaction of the target lipid assay reagent may be employed in combination with the polycyclic polyoxyalkylene derivative, that acts on a specific lipoprotein.

The buffer to be employed may be Good's buffer, phosphoric acid, tris, phthalic acid, a citric acid salt, a buffer solution which is generally employed within a pH range of 5 to 9, and any substance exhibiting buffering effects within this pH range. No particular limitations are imposed on the amount of the buffer to be employed, but the amount is preferably 0.005 M to 2 M, particularly preferably 0.01 to 1 M. The reactivity of the polycyclic polyoxyalkylene derivative employed in the present invention does not depend on the buffer solution. The aforementioned two steps may be carried out at the same reaction temperature or different reaction temperatures. The reaction temperature is preferably a temperature at which the reagent of the present invention is in a solution form (e.g., 10 to 40° C.).

Examples of the surfactant employed in combination with the polycyclic polyoxyalkylene derivative include a surfactant employed for assaying a target lipid containing in a specific lipoprotein after a lipid contained in lipoproteins other than a specific lipoprotein is pretreated with the polycyclic polyoxyalkylene derivative; and a surfactant for controlling the reaction of the target lipid assay reagent through adjustment of enzymatic activity without losing the specificity of assay of the target lipid. Unlike the case of the polycyclic polyoxyalkylene derivative, which is employed in the specificity determining step, the surfactant employed in combination with the derivative is not required to exhibit specificity to the target lipid. Examples of the surfactant which may be employed include a surfactant having no aryl groups, and a surfactant having only one aryl group. The surfactant may be a nonionic or ionic surfactant. Examples of the nonionic surfactant which may be employed include a polyoxyethylene alkyl ether having no aryl groups, a polyoxyethylene-polyoxypropylene condensate having no aryl groups, and a polyoxyethylene alkylphenyl ether having one phenyl group. An example of the polyoxyethylene alkyl ether includes Emulgen 709 (product of Kao Corporation); An example of the polyoxyethylene alkylphenyl ether includes Triton X100 (product of Sigma); and an example of the polyoxyethylene-polyoxypropylene condensate includes Pluronic F-108 (product of Asahi Denka Co., Ltd.). An example of the ionic surfactant which may be employed include bile acid. The amount of such a surfactant to be employed preferably 0.0001 to 5%, particularly preferably 0.001 to 5%.

No particular limitations are imposed on the method for detecting the target lipid after addition of the aforementioned lipid assay enzyme reagent. Examples of the detection method which may be employed include an absorbance analysis employing peroxidase or diaphorase in combination with a chromogen; a method in which a coenzyme or hydrogen peroxide is directly detected; and a method for determining oxidation/reduction of a metal, etc. The reagent of the present invention may be provided in a solution form, a dry form, or a gel form. The reagent may be provided in a variety of product forms. For example, the reagent may be stored in a glass vial or a plastic container, or applied to or impregnated into various insoluble carriers, such as particulate or spherical carriers formed of latex, glass, or colloid, plate-like carriers formed of semiconductor or glass, film-like carriers formed of paper or nitrocellulose, and fibrous carriers.

In the case of assay of HDL cholesterol or LDL cholesterol by means of the method of the present invention, HDL or LDL is reacted with, for example, cholesterol oxidase and cholesterol esterase in the presence of a polycyclic polyoxyalkylene derivative. Alternatively, cholesterol contained in lipoproteins other than HDL or LDL may be pretreated in the presence of a polycyclic polyoxyalkylene derivative, and, in the next step, the remaining HDL or LDL may be reacted with cholesterol oxidase and cholesterol esterase.

In the case of assay of HDL triglyceride or LDL triglyceride, free glycerol is pretreated in a first step, and lipoprotein lipase is applied in a second step, followed by reaction of the HDL or LDL with a generally employed reagent for assaying triglyceride. In this case, a polycyclic polyoxyalkylene derivative may be employed in the first step or the second step. Preferred modes of the triglyceride assay method include a method for assaying triglyceride contained in a specific lipoprotein, which method includes a step of pretreating free glycerol such that the glycerol does not participate in reaction, and a step of applying lipoprotein lipase to act on a specific lipoprotein, wherein the lipoprotein lipase is reacted with triglyceride contained in the specific lipoprotein in the presence of a polycyclic polyoxyalkylene derivative; and a method for assaying triglyceride contained in a specific lipoprotein, which method includes a step of pretreating free glycerol such that the glycerol does not participate in reaction, and a step of applying lipoprotein lipase to act on a specific lipoprotein, wherein the free glycerol and triglyceride contained in lipoproteins other than the specific lipoprotein are pretreated in the presence of a polycyclic polyoxyalkylene derivative having an HLB of 12 to 15. When free glycerol contained in a sample is assayed in a step apart from the aforementioned steps, or when the amount of glycerol in the sample is negligibly small as compared with the amount of triglyceride contained in the specific lipoprotein, the step of pretreating the free glycerol or the applicable reagents may be omitted.

The aforementioned fundamental procedures have generally been employed as techniques for assaying, for example, HDL cholesterol, LDL cholesterol, and triglyceride contained in serum.

EXAMPLES

The present invention will next be described in more detail by way of Examples, which should not be construed as limiting the invention thereto.

In the below-described Examples, a polycyclic polyoxyalkylene derivative may be referred to as a "surfactant of the present invention."

Example 1

Assay of HDL Cholesterol

HDL cholesterol was assayed by means of the method of the present invention by use of a Hitachi 7170 automatic analyzer, and the thus-assayed HDL cholesterol level was compared with the HDL cholesterol level obtained by use of a commercially available reagent for assaying HDL cholesterol. In this Example, 15 human serum samples were employed. In the method of the present invention, a reagent (240 µL) containing 0.01% 4-aminoantipyrine and 100 mM PIPES buffer solution (pH 6.5) was added to a serum sample (2.4 µL), followed by heating at 37° C. for five minutes; and subsequently, to the resultant mixture was added a reagent (80 µL) containing 1% a surfactant of the present invention, 1 unit/mL cholesterol oxidase (Oriental Yeast Co., Ltd.), 1 unit/mL cholesterol esterase (Asahi Kasei Corporation), 1 unit/mL peroxidase, 0.04% N,N-disulfobutyl-m-toluidine, and 100 mM PIPES buffer solution (pH 6.5), followed by measurement of the amount of change in absorbance at 37° C. at secondary wavelength 700 nm/primary wavelength 600 nm. Cholestest N HDL (product of Daiichi Pure Chemicals Co., Ltd.) was employed as the commercial HDL cholesterol assay reagent, and HDL cholesterol was assayed by means of the method described in the attached manual. The correlation coefficient between the thus-obtained HDL cholesterol level and the HDL cholesterol level obtained by means of the method of the present invention was obtained. The results are shown in Table 1. As shown in Table 1, a favorable correlation is observed between the HDL cholesterol level obtained by means of the method of the present invention and the HDL cholesterol level obtained by means of the conventional method (autoanalysis method). Furthermore, in a manner similar to that described above, HDL cholesterol was assayed by use of a surfactant containing one phenyl group (Triton X100) (i.e., comparative example) in place of the surfactant of the present invention.

TABLE 1

Comparison of correlation coefficient

| Surfactant | Correlation coefficient |
| --- | --- |
| Pionin D-6112W | 0.90 |
| Pionin D-6115X | 0.81 |
| Pionin D-6320 | 0.84 |
| Pionin D-640 | 0.79 |
| Newkalgen FS-12 | 0.89 |
| Sanmol 2SP-180 | 0.89 |
| Newcol 610 | 0.88 |
| Newcol 710 | 0.79 |
| Newcol 710F | 0.79 |
| Newcol 714 | 0.81 |
| Newcol 714F | 0.84 |
| Newcol 2600FB | 0.92 |
| Newcol 2608F | 0.92 |
| Newcol 2609 | 0.89 |
| Pegnol 005 | 0.92 |
| Emulgen A90 | 0.94 |
| Airrol T1500 | 0.88 |
| Triton X100 (Comparative Example) | 0.68 |

Example 2

Assay of HDL Cholesterol

HDL cholesterol was assayed by means of the method of the present invention by use of a Hitachi 7170 automatic analyzer, and the thus-assayed HDL cholesterol level was compared with the HDL cholesterol level obtained by use of a commercially available reagent for assaying HDL cholesterol. In this Example, 15 human serum samples were employed. In the method of the present invention, a reagent (240 µL) containing 0.01% 4-aminoantipyrine, 45 µM digitonin (Tokyo Kasei Kogyo Co., Ltd.), and 100 mM PIPES buffer solution (pH 6.5) was added to a serum sample (2.4 µL), followed by heating at 37° C. for five minutes; and subsequently, to the resultant mixture was added a reagent (80 µL) containing 1% a surfactant of the present invention, 1 unit/mL cholesterol oxidase (Oriental Yeast Co., Ltd.), 1 unit/mL cholesterol esterase (Asahi Kasei Corporation), 1 unit/mL peroxidase, 0.04% N,N-disulfobutyl-m-toluidine, and 100 mM PIPES buffer solution (pH 6.5), followed by measurement of the amount of change in absorbance at 37° C. at secondary wavelength 700 nm/primary wavelength 600 nm. Cholestest N HDL (product of Daiichi Pure Chemicals Co., Ltd.) was employed as the commercial HDL cholesterol assay reagent, and HDL cholesterol was assayed by means of the method described in the attached manual. The correlation coefficient between the thus-obtained HDL cholesterol level and the HDL cholesterol level obtained by means of the method of the present invention was obtained. The results are shown in Table 2. As shown in Table 2, a favorable correlation is observed between the HDL cholesterol level obtained by means of the method of the present invention and the HDL cholesterol level obtained by means of the conventional method (autoanalysis method). Furthermore, in a manner similar to that described above, HDL cholesterol was assayed by use of a surfactant containing one phenyl group (Triton X100) (i.e., comparative example) in place of the surfactant of the present invention.

TABLE 2

Comparison of correlation coefficient

| Surfactant | Correlation coefficient |
|---|---|
| Pionin D-6115X | 0.92 |
| Pionin D-6115Z | 0.93 |
| Pionin D-640 | 0.91 |
| Sorpol T-26 | 0.93 |
| Newcol 714 | 0.94 |
| Newcol 714F | 0.95 |
| Newcol 740 | 0.88 |
| Airrol T1500 | 0.98 |
| Triton X100 (Comparative Example) | 0.67 |

Example 3

Assay of HDL Cholesterol

HDL cholesterol was assayed by means of the method of the present invention by use of a Hitachi 7170 automatic analyzer, and the thus-assayed HDL cholesterol level was compared with the HDL cholesterol level obtained by use of a commercially available reagent for assaying HDL cholesterol. In this Example, 15 human serum samples were employed. In the method of the present invention, a reagent (240 µL) containing 0.01% 4-aminoantipyrine, 0.04% sodium phosphotungstate (Kishida Chemical Co., Ltd.), 0.2% magnesium chloride, and 100 mM PIPES buffer solution (pH 6.5) was added to a serum sample (2.4 µL), followed by heating at 37° C. for five minutes; and subsequently, to the resultant mixture was added a reagent (80 µL) containing 1% a surfactant of the present invention, 1 unit/mL cholesterol oxidase (Oriental Yeast Co., Ltd.), 1 unit/mL cholesterol esterase (Asahi Kasei Corporation), 1 unit/mL peroxidase, 0.04% N,N-disulfobutyl-m-toluidine, and 100 mM PIPES buffer solution (pH 6.5), followed by measurement of the amount of change in absorbance at 37° C. at secondary wavelength 700 nm/primary wavelength 600 nm. Cholestest N HDL (product of Daiichi Pure Chemicals Co., Ltd.) was employed as the commercial HDL cholesterol assay reagent, and HDL cholesterol was assayed by means of the method described in the attached manual. The correlation coefficient between the thus-obtained HDL cholesterol level and the HDL cholesterol level obtained by means of the method of the present invention was obtained. The results are shown in Table 3. As shown in Table 3, a favorable correlation is observed between the HDL cholesterol level obtained by means of the method of the present invention and the HDL cholesterol level obtained by means of the conventional method (autoanalysis method). Furthermore, in a manner similar to that described above, HDL cholesterol was assayed by use of a surfactant containing one phenyl group (Triton X100) (i.e., comparative example) in place of the surfactant of the present invention.

TABLE 3

Comparison of correlation coefficient

| Surfactant | Correlation coefficient |
|---|---|
| Sorpol T-15 | 0.90 |
| Sorpol T-20 | 0.84 |
| Newcol 714 | 0.87 |
| Newcol 714F | 0.88 |
| Airrol T1500 | 0.93 |
| Triton X100 (Comparative Example) | 0.73 |

Example 4

Assay of LDL Cholesterol

LDL cholesterol was assayed by means of the method of the present invention by use of a Hitachi 7170 automatic analyzer, and the thus-assayed LDL cholesterol level was compared with the LDL cholesterol level obtained by use of a commercially available reagent for assaying LDL cholesterol. In this Example, 15 human serum samples were employed. In the method of the present invention, a first reagent (240 µL) containing 1 unit/mL cholesterol oxidase (Toyobo Co., Ltd.), 1 unit/mL cholesterol esterase (Asahi Kasei Corporation), 1 unit/mL peroxidase, 0.02% N,N-disulfobutyl-m-toluidine, 100 mM PIPES buffer solution (pH 6.5), and 1% a surfactant of the present invention was added to a serum sample (2.4 µL), followed by heating at 37° C. for 10 minutes; and subsequently, to the resultant mixture was added a reagent (80 µL) containing 0.02% 4-aminoantipyrine, 100 mM PIPES buffer solution (pH 6.5), and 1% Emulgen 709, followed by measurement of the amount of change in absorbance at 37° C. at secondary wavelength 660 nm/primary wavelength 546 nm. Cholestest LDL (product of Daiichi Pure Chemicals Co., Ltd.) was employed as the commercial LDL cholesterol assay reagent, and LDL cholesterol was assayed by means of the method described in the attached manual. The results are shown in Table 4. As shown in Table 4, a favorable correlation is observed between the LDL cholesterol level obtained by means of the method of the present invention and the LDL cholesterol level obtained by means of the conventional method (autoanalysis method). Furthermore, in a manner similar to that described above, LDL cholesterol was assayed by use of a surfactant containing one phenyl group (Triton X100) (i.e., comparative example) in place of the surfactant of the present invention.

TABLE 4

Comparison of correlation coefficient

| Surfactant | Correlation coefficient |
|---|---|
| Pionin D-6115X | 0.98 |
| Pionin D-6115Z | 0.97 |
| Pionin D-640 | 0.96 |
| Sorpol T-15 | 0.92 |

TABLE 4-continued

Comparison of correlation coefficient

| Surfactant | Correlation coefficient |
|---|---|
| Sorpol T-20 | 0.99 |
| Sanmol 2SP-180 | 0.99 |
| Newcol 610 | 0.99 |
| Newcol 710 | 0.99 |
| Newcol 710F | 0.99 |
| Newcol 714 | 0.98 |
| Newcol 714F | 0.98 |
| Newcol 740 | 0.96 |
| Newcol 2608F | 0.91 |
| Pegnol 005 | 0.99 |
| Emulgen A90 | 0.99 |
| Airrol T1500 | 0.95 |
| Triton X100 (Comparative Example) | 0.74 |

Example 5

Assay of HDL Cholesterol and LDL Cholesterol

HDL cholesterol was assayed by means of the method of the present invention by use of a Hitachi 7170 automatic analyzer, and the thus-assayed HDL cholesterol level was compared with the HDL cholesterol level obtained by use of a commercially available reagent for assaying HDL cholesterol. In this Example, 50 serum samples were employed. In the method of the present invention, a reagent (240 μL) containing 1 unit/mL cholesterol oxidase (Toyobo Co., Ltd.), 1 unit/mL peroxidase, 0.02% N,N-disulfobutyl-m-toluidine, 0.2 mM flufenamic acid (Sigma), 50 mM NaCl, and 50 mM Bis-Tris buffer solution (pH 6) was added to a serum sample (2.4 μL), followed by heating at 37° C. for five minutes; and subsequently, to the resultant mixture was added a reagent (80 μL) containing 1 unit/mL cholesterol esterase (Asahi Kasei Corporation), 1% Pegnol 005, 0.02% 4-aminoantipyrine, and 50 mM Bis-Tris buffer solution (pH 6), followed by measurement of the amount of change in absorbance at 37° C. at secondary wavelength 700 nm/primary wavelength 600 nm. Cholestest N HDL (product of Daiichi Pure Chemicals Co., Ltd.) was employed as the commercial HDL cholesterol assay reagent, and HDL cholesterol was assayed by means of the method described in the attached manual. The results are shown in FIG. 1. As shown in FIG. 1, a favorable correlation is observed between the HDL cholesterol level obtained by means of the method of the present invention and the HDL cholesterol level obtained by means of the conventional method (autoanalysis method) (correlation coefficient (r)=0.999).

Figure 2:
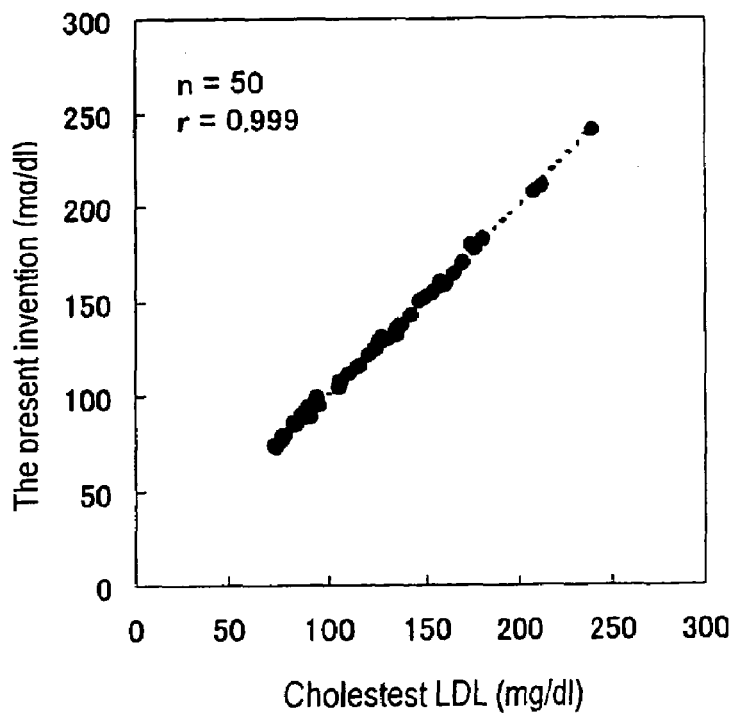
FIG. 2 shows the correlation between the method of the present invention and a conventional method (by use of Cholestest LDL).

Subsequently, LDL cholesterol was assayed by means of the method of the present invention by use of a Hitachi 7170 automatic analyzer, and the thus-assayed LDL cholesterol level was compared with the LDL cholesterol level obtained by use of a commercially available reagent for assaying LDL cholesterol. In this Example, 50 serum samples were employed. In the method of the present invention, a first reagent (240 μL) containing 1 unit/mL cholesterol oxidase (Asahi Kasei Corporation), 1 unit/mL cholesterol esterase (Asahi Kasei Corporation), 1% Pegnol 005 (Toho Chemical Industry Co., Ltd.), 1 unit/mL peroxidase, 0.01% 4-aminoantipyrine, 200 mm NaCl, and 50 mM MES buffer solution (pH 6.5) was added to a serum sample (2.4 μL), followed by heating at 37° C. for five minutes; and subsequently, to the resultant mixture was added a reagent (80 μL) containing 0.04% N,N-disulfobutyl-m-toluidine, 1% Emulgen 709, and 50 mM MES buffer solution (pH 6.5), followed by measurement of the amount of change in absorbance at 37° C. at secondary wavelength 660 nm/primary wavelength 546 nm. Cholestest LDL (product of Daiichi Pure Chemicals Co., Ltd.) was employed as the commercial LDL cholesterol assay reagent, and LDL cholesterol was assayed by means of the method described in the attached manual. The results are shown in FIG. 2. As shown in FIG. 2, a favorable correlation is observed between the LDL cholesterol level obtained by means of the method of the present invention and the LDL cholesterol level obtained by means of the conventional method (autoanalysis method) (correlation coefficient (R)=0.999).

The above-described results reveal that a surfactant of the present invention can be employed for assay of lipids contained in a plural number of specific lipoproteins.

Example 6

Assay of HDL cholesterol and LDL cholesterol

Figure 3:
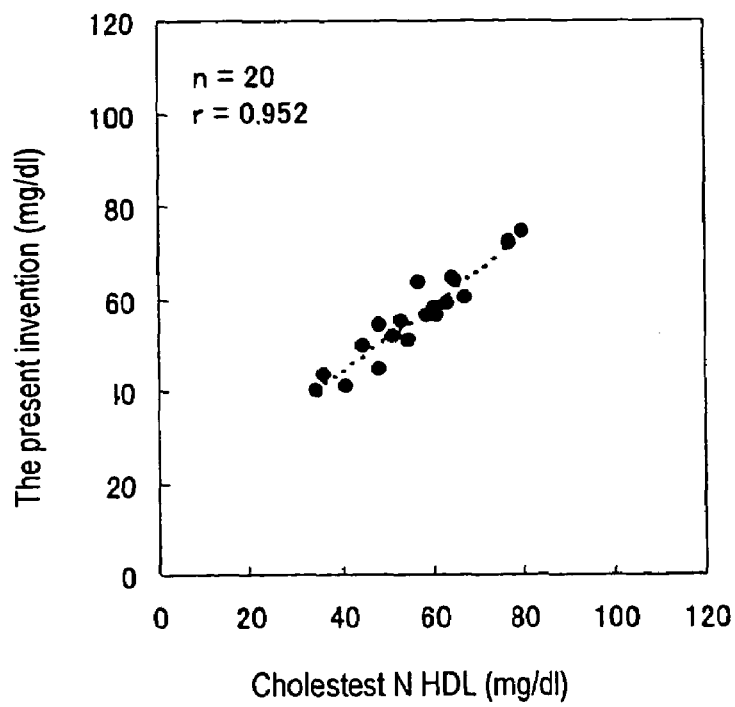
FIG. 3 shows the correlation between the method of the present invention and a conventional method (by use of Cholestest N HDL).

HDL cholesterol was assayed by means of the method of the present invention by use of a Hitachi 7170 automatic analyzer, and the thus-assayed HDL cholesterol level was compared with the HDL cholesterol level obtained by use of a commercially available reagent for assaying HDL cholesterol. In this Example, 20 human serum samples were employed. In the method of the present invention, a reagent (240 μL) containing 0.01% 4-aminoantipyrine and 100 mM PIPES buffer solution (pH 6.5) was added to a serum sample (2.4 μL), followed by heating at 37° C. for five minutes; and subsequently, to the resultant mixture was added a reagent (80 μL) containing 1 unit/mL cholesterol oxidase (Oriental Yeast Co., Ltd.), 1 unit/mL cholesterol esterase (Asahi Kasei Corporation), 1% Emulgen A90, 1 unit/mL peroxidase, 0.04% N,N-disulfobutyl-m-toluidine, and 100 mM PIPES buffer solution (pH 6.5), followed by measurement of the amount of change in absorbance at 37° C. at secondary wavelength 700 nm/primary wavelength 600 nm. Cholestest N HDL (product of Daiichi Pure Chemicals Co., Ltd.) was employed as the commercial HDL cholesterol assay reagent, and HDL cholesterol was assayed by means of the method described in the attached manual. The results are shown in FIG. 3. As shown in FIG. 3, a favorable correlation is observed between the HDL cholesterol level obtained by means of the method of the present invention and the HDL cholesterol level obtained by means of the conventional method (autoanalysis method) (correlation coefficient (r)=0.952).

Figure 4:
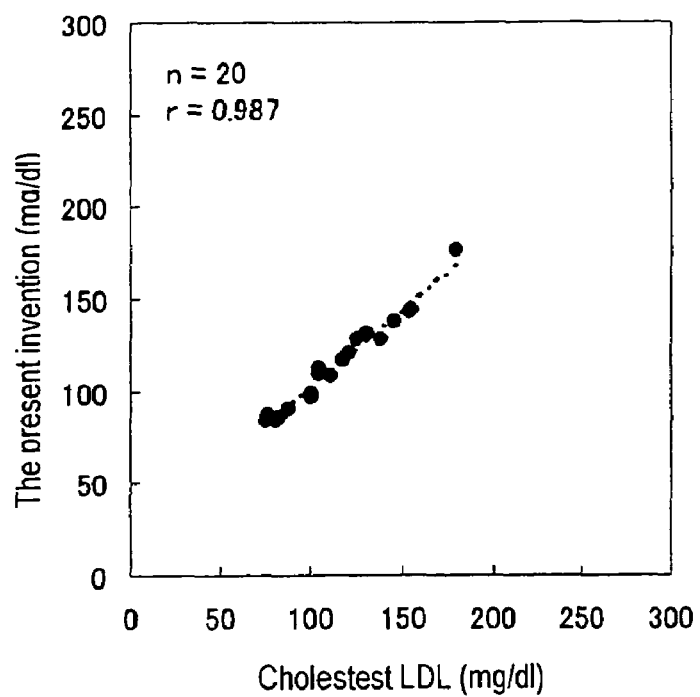
FIG. 4 shows the correlation between the method of the present invention and a conventional method (by use of Cholestest LDL).

Subsequently, LDL cholesterol was assayed by means of the method of the present invention by use of a Hitachi 7170 automatic analyzer, and the thus-assayed LDL cholesterol level was compared with the LDL cholesterol level obtained by use of a commercially available reagent for assaying LDL cholesterol. In this Example, 20 human serum samples were employed. In the method of the present invention, a reagent (240 μL) containing 1 unit/mL cholesterol oxidase (Toyobo Co., Ltd.), 1 unit/mL cholesterol esterase (Asahi Kasei Corporation), 1 unit/mL peroxidase, 0.02% N,N-disulfobutyl-m-toluidine, 100 mM PIPES buffer solution (pH 6.5), and 1% Emulgen A90 was added to a serum sample (2.4 μL), followed by heating at 37° C. for 10 minutes; and subsequently, to the resultant mixture was added a reagent (80 μL) containing 0.02% 4-aminoantipyrine, 100 mM PIPES buffer solution (pH 6.5), and 1% Emulgen 709, followed by measurement of the amount of change in absorbance at 37° C. at secondary wavelength 660 nm/primary wavelength 546 nm. Cholestest LDL (product of Daiichi Pure Chemicals Co., Ltd.) was employed as the commercial LDL cholesterol assay reagent, and LDL cholesterol was assayed by means of the method described in the attached manual. The results are shown in FIG. 4. As shown in FIG. 4, a favorable correlation is observed between the LDL cholesterol level obtained by means of the method of the present invention and the LDL cholesterol level obtained by means of the conventional method (autoanalysis method) (correlation coefficient (r)=0.987).

The above-described results reveal that a surfactant of the present invention can be employed for assay of lipids contained in a plural number of specific lipoproteins.

Example 7

Assay of LDL Cholesterol

LDL cholesterol was assayed by means of the method of the present invention employing different LDL cholesterol assay reagents prepared by use of various buffer solutions, and the thus-assayed LDL cholesterol levels were compared with one another. LDL cholesterol was assayed by use of a Hitachi 7170 automatic analyzer. In this Example, 15 human serum samples were employed. In the method of the present invention, a reagent (240 µL) containing 1 unit/mL cholesterol oxidase (Toyobo Co., Ltd.), 1 unit/mL cholesterol esterase (Asahi Kasei Corporation), 1 unit/mL peroxidase, 0.02% N,N-disulfobutyl-m-toluidine, 1% Pegnol 005, and a buffer solution (100 mM) was added to a serum sample (2.4 µL), followed by heating at 37° C. for five minutes; and subsequently, to the resultant mixture was added a reagent (80 µL) containing 0.02% 4-aminoantipyrine, 1% Emulgen 709, and a buffer solution (100 mM), followed by measurement of the amount of change in absorbance at 37° C. at secondary wavelength 660 nm/primary wavelength 546 nm. Cholestest LDL (product of Daiichi Pure Chemicals Co., Ltd.) was employed as the commercial LDL cholesterol assay reagent, and LDL cholesterol was assayed by means of the method described in the attached manual. The results are shown in Table 5. As shown in Table 5, regardless of the type of a buffer solution, a favorable correlation is observed between the LDL cholesterol level obtained by means of the method of the present invention and the LDL cholesterol level obtained by means of the conventional method (autoanalysis method).

TABLE 5

Comparison of correlation coefficient

| Buffer solution (pH) | Correlation coefficient |
| --- | --- |
| PIPES (6.5) | 0.998 |
| MES (6.5) | 0.997 |
| Phosphoric acid (6.5) | 0.997 |
| Maleic acid (6.5) | 0.998 |
| Phthalic acid (6.0) | 0.996 |

Example 8

Assay of LDL Triglyceride

Figure 5:
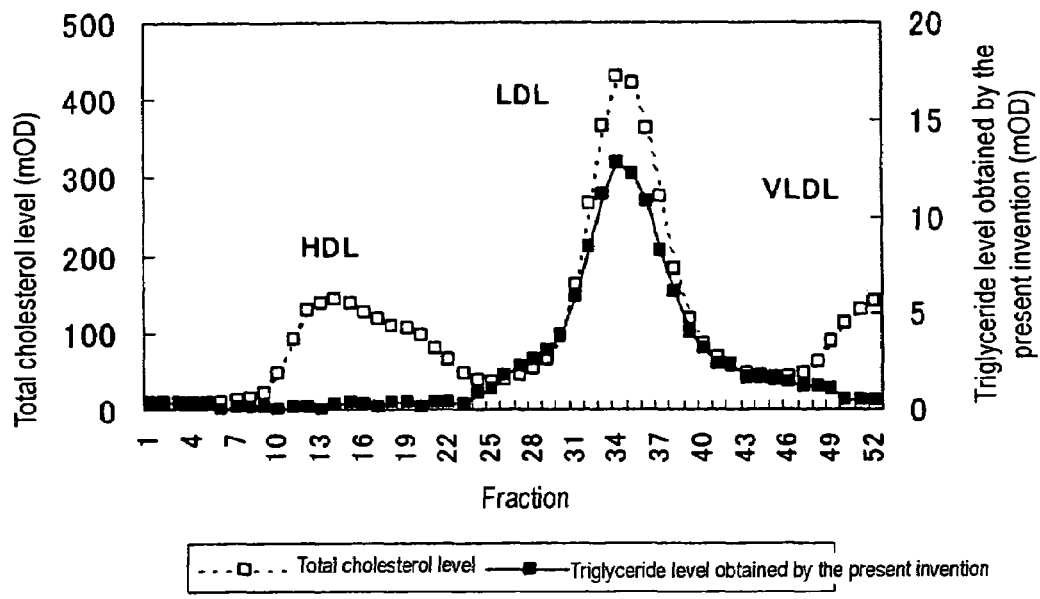
FIG. 5 shows the results of assay of LDL triglyceride by means of the method of the present invention.

A serum sample was separated by ultracentrifugation to fractionate the lipoproteins, and total cholesterol in each of the fractions was assayed. The thus-obtained data were plotted as shown in FIG. 5. In addition, triglyceride in the same sample was assayed by means of the method of the present invention, and the thus-obtained data were plotted as shown in FIG. 5. The triglyceride was assayed by use of a Hitachi 7150 automatic analyzer, and the total cholesterol was assayed by use of Pureauto S T-CHO (product of Daiichi Pure Chemicals Co., Ltd.). In the method of the present invention for assaying LDL triglyceride, a first reagent (300 µL) containing 0.5 units/mL glycerol kinase (Asahi Kasei Corporation), 3 units/mL glycerol 3-phosphate oxidase (Toyobo Co., Ltd.), 1.5 units/mL peroxidase (Toyobo Co., Ltd.), 1 unit/mL LPL (Toyobo Co., Ltd.), 1% Pegnol 005 (Toho Chemical Industry Co., Ltd.), 3 mM magnesium chloride, 0.5 mM calcium chloride, 2.5 mM ATP, 0.02% ethylsulfobutyl-m-toluidine, and 50 mM MES buffer solution (pH 6.3) was added to a serum sample (3 µL), followed by heating at 37° C. for five minutes; and subsequently, to the resultant mixture was added a reagent (100 µL) containing 0.01% 4-aminoantipyrine, 1% Emulgen 709, and 50 mM MES buffer solution (pH 6.3), followed by measurement of the amount of change in absorbance at 37° C. at secondary wavelength 700 nm/primary wavelength 546 nm. As shown in FIG. 5, the method of the present invention specifically assays TG in LDL.

Example 9

Assay of HDL Triglyceride

Figure 6:
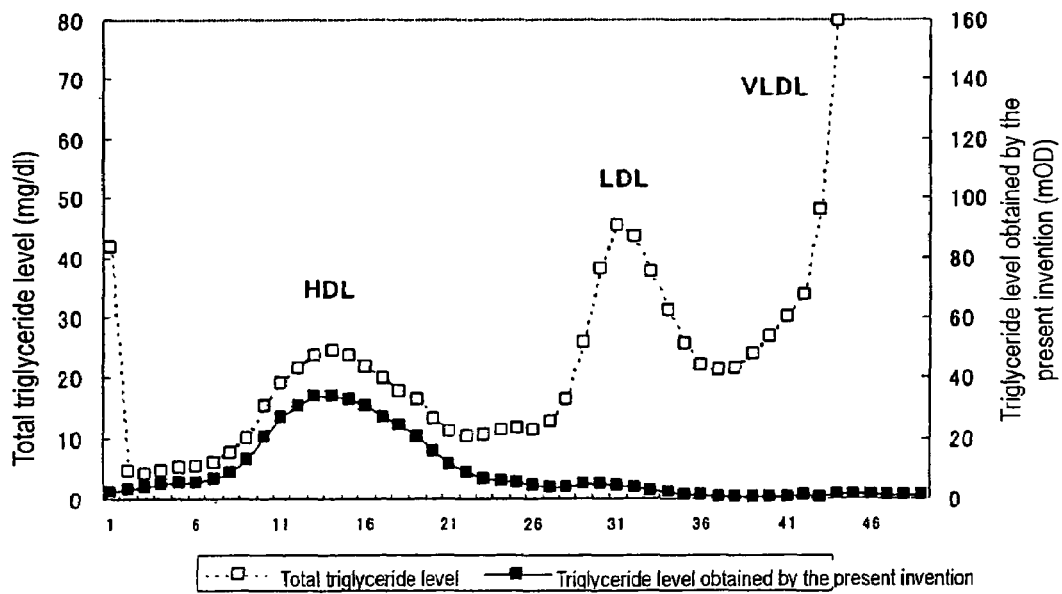
FIG. 6 shows the results of assay of HDL triglyceride by means of the method of the present invention.

A serum sample was separated by ultracentrifugation to fractionate the lipoproteins, and total triglyceride in each of the fractions was assayed. The thus-obtained data were plotted as shown in FIG. 6. In addition, triglyceride in the same sample was assayed by means of the method of the present invention by use of a Hitachi 7170 automatic analyzer, and the thus-obtained data were plotted as shown in FIG. 6. The total triglyceride was assayed by use of Pureauto S TG-N (product of Daiichi Pure Chemicals Co., Ltd.). In the method of the present invention for assaying HDL triglyceride, a first reagent (210 µL) containing 3 units/mL glycerol kinase (Asahi Kasei Corporation), 3 units/mL glycerol 3-phosphate oxidase (Toyobo Co., Ltd.), 500 units/mL catalase, 3 mM magnesium chloride, 3 mM ATP, 2 mM ethylsulfobutyl-m-toluidine, and 100 mM PIPES buffer solution (pH 7) was added to a serum sample (2.8 µL), followed by heating at 37° C. for five minutes; and subsequently, to the resultant mixture was added a reagent (70 µL) containing 500 units/mL lipase (Asahi Kasei Corporation), 1 unit/mL monoglyceride lipase (Asahi Kasei Corporation), 10 units/mL peroxidase (Toyobo Co., Ltd.), 1.5% Pegnol 005 (Toho Chemical Industry Co., Ltd.), 0.04% 4-aminoantipyrine, 1 mM calcium chloride, and 100 mM PIPES buffer solution (pH 7), followed by measurement of the amount of change in absorbance at 37° C. at secondary wavelength 700 nm/primary wavelength 546 nm. As shown in FIG. 6, the method of the present invention specifically assays TG in HDL.

Example 10

Relation Between the HLB of a Surfactant and Correlation Coefficient

Figure 7:
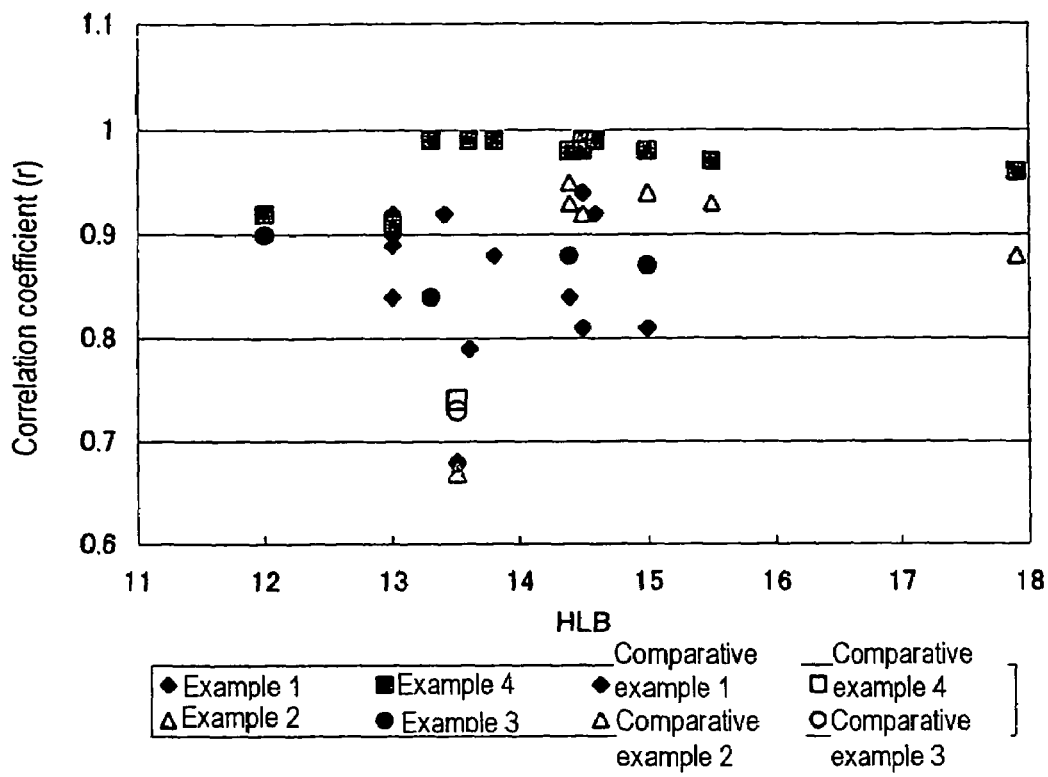
FIG. 7 shows the relation between the HLB of surfactants of the present invention and correlation coefficients.

Although the HLB of a surfactant of the present invention is not a particularly important factor, it is preferably 12 or more. FIG. 7 shows the relation between correlation coefficients described in Examples 1 through 4 and the HLB of surfactants of the present invention. FIG. 7 indicates that no correlation is observed between the HLB of surfactants and the correlation coefficients.

Example 11

Figure 8:
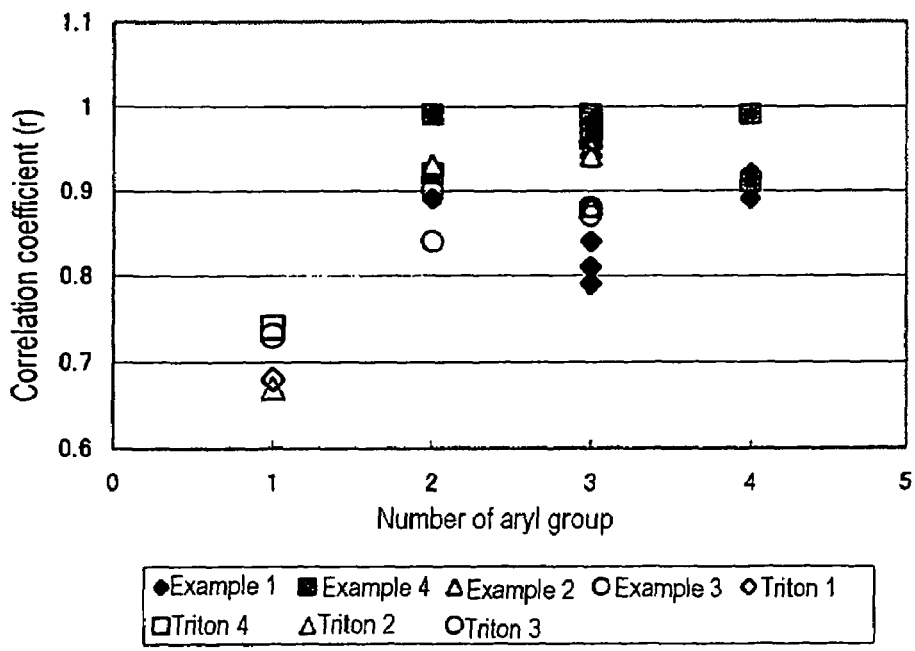
FIG. 8 shows the relation between the number of aryl groups contained in surfactants of the present invention and correlation coefficients.

Relation between the Number of Aryl Groups Contained in a Surfactant and Correlation Coefficient One of the characteristic features of a surfactant of the present invention is that it has two or more aryl groups (Table 6). FIG. 8 shows the relation between correlation coefficients described in Examples 1 through 4 and the number of aryl groups contained in surfactants of the present invention. Among surfactants of the present invention, condensate-type of surfactants are omitted. FIG. 8 indicates that, in the case where two or more aryl groups are contained in a surfactant, the correlation coefficient becomes higher, as compared with the case of a surfactant containing one aryl group (i.e., comparative example). As used herein, the number of aryl group is represented by the number of phenyl group, which is a typical example of a group having a benzene ring that is a structural feature common to aryl groups.

TABLE 6

Number of aryl groups contained in surfactants of the present invention

| Surfactant of the present invention | | Number of aryl group (number of phenyl group) |
|---|---|---|
| Sorpol | T-15 | 2 |
| Sorpol | T-20 | 2 |
| Sorpol | T-26 | 2 |
| Sanmol | 2SP-180 | 2 |
| Newcol | 610 | 3 |
| Newcol | 710 | 3 |
| Newcol | 710(F) | 3 |
| Newcol | 714 | 3 |
| Newcol | 714F | 3 |
| Newcol | 740 | 3 |
| Emulgen | A90 | 3 |
| Pegnol | 005 | 4 |
| Newcol | 2608F | 4 |
| Newcol | 2600FB | 4 |
| Newcol | 2609 | 4 |
| Comparative Example | | |
| Triton | X100 | 1 |

The invention claimed is:

1. A method for assaying HDL cholesterol in a sample, comprising:
   determining the specificity of an assay for HDL cholesterol, and
   assaying HDL cholesterol using said assay;
   wherein a mixture of a plurality of polycyclic polyoxyalkylene derivatives is employed at least in the specificity determining step, said mixture having an HLB of 14.1 to 18, and
   wherein the polycyclic polyoxyalkylene derivatives are nonionic surfactants selected from the group consisting of polyoxyalkylene polycyclic phenyl ether, polyoxyethylene tribenzylphenyl ether, polyoxyalkylene polystyrylphenyl ether, polyoxyalkylene phenylphenol ether, polyoxyalkylene polystyrylphenyl ether condensate, polyoxyalkylene alkylphenyl ether condensate, polyoxyalkylene styrylated phenyl ether, and polyoxyalkylene allylphenyl ether.

2. The method of claim 1, wherein said mixture has an HLB of 14.3 to 18.

3. The method of claim 1, wherein said mixture is in solution form.

4. A method for assaying HDL cholesterol in a sample, comprising:
   determining the specificity of an assay for HDL cholesterol, and
   assaying HDL cholesterol using said assay;
   wherein at least one polycyclic polyoxyalkylene derivative having an HLB of 14.1 to 18 and being selected from the group consisting of polyoxyalkylene polycyclic phenyl ether, polyoxyethylene tribenzylphenyl ether, polyoxyalkylene polystyrylphenyl ether; polyoxyalkylene phenylphenol ether, polyoxyalkylene polystyrylphenyl ether condensate, polyoxyalkylene alkylphenyl ether condensate, polyoxyalkylene styrylated phenyl ether, and polyoxyalkylene allylphenyl ether is employed at least in the specificity determining step.

5. The method of claim 4, wherein said polycyclic polyoxyalkylene derivative has an HLB of 14.3 to 18.

6. The method in accordance with claim 4, wherein the polycyclic polyoxyalkylene derivative is in a solution form.

7. A method for determining the amount of HDL cholesterol in a sample, comprising:
   determining the specificity of an assay for HDL cholesterol by pretreating lipids other than HDL cholesterol in a biological sample to obtain a pretreated reaction mixture containing HDL cholesterol,
   reacting the HDL cholesterol in said pretreated reaction mixture with an enzyme that releases cholesterol from said HDL cholesterol, and
   assaying the cholesterol,
   thereby determining the amount of HDL cholesterol in said biological sample;
   wherein at least the determining the specificity of the assay is performed in the presence of at least one nonionic polycyclic polyoxyalkylene surfactant having an HLB of 14.1 to 18 selected from the group consisting of polyoxyalkylene polycyclic phenyl ether, polyoxyethylene tribenzylphenyl ether, polyoxyalkylene polystyrylphenyl ether, polyoxyalkylene phenylphenol ether, polyoxyalkylene polystyrylphenyl ether condensate, polyoxyalkylene alkylphenyl ether condensate, polyoxyalkylene styrylated phenyl ether, and polyoxyalkylene allylphenyl ether.

8. The method of claim 7, wherein a mixture of a plurality of the polycyclic polyoxyalkylene surfactants is employed at least in the specificity determining step, said mixture having an HLB of 14.1 to 18.

9. The method of claim 7, wherein said polycyclic polyoxyalkylene surfactant is in a solution form.

10. The method of claim 7, wherein said biological sample is blood, serum or plasma.

11. The method of claim 7, wherein said pretreated reaction mixture containing HDL cholesterol is produced without centrifugation of said biological sample.

12. The method of claim 7, wherein said enzyme that releases cholesterol from HDL cholesterol is an esterase.

13. The method of claim 12, wherein said esterase is employed in combination with an enzyme other than the esterase, a coenzyme, or a color coupler to assay cholesterol.

14. The method of claim 13, wherein said HDL cholesterol is assayed by measuring the amount of change in absorbance at 37° C. at secondary wavelength 700 nm/primary wavelength 600 nm.

* * * * *